United States Patent [19]

Gilbert

[11] 4,094,967

[45] June 13, 1978

[54] IODINE-POLYVINYLPYRROLIDONE SOLID PRODUCT AND METHOD OF PREPARATION

[75] Inventor: Joseph G. Gilbert, Lighthouse Point, Fla.

[73] Assignee: Allor Foundation, Boston, Mass.

[21] Appl. No.: 735,088

[22] Filed: Oct. 22, 1976

[51] Int. Cl.$^2$ .................... A01N 11/00; A61K 31/79; A61K 33/18

[52] U.S. Cl. ...................... 424/28; 424/80; 424/150

[58] Field of Search ............................ 424/80, 150, 28

[56] References Cited

U.S. PATENT DOCUMENTS

| | | | |
|---|---|---|---|
| 2,706,701 | 4/1955 | Beller et al. | 424/80 |
| 2,826,532 | 3/1958 | Hosmer | 424/80 |
| 2,900,305 | 8/1959 | Siggia | 424/80 |
| 3,028,300 | 4/1962 | Cantor et al. | 424/80 |
| 3,764,669 | 10/1973 | Santorelli | 424/80 |
| 3,777,016 | 12/1973 | Gilbert | 424/80 |
| 3,898,326 | 8/1975 | Cantor et al. | 424/80 |

*Primary Examiner*—Albert T. Meyers
*Assistant Examiner*—D. W. Robinson
*Attorney, Agent, or Firm*—Rines and Rines, Shapiro and Shapiro

[57] ABSTRACT

This disclosure relates to novel iodine-polyvinylpyrrolidone products in which, by novel preparation methods, the iodine is adherently bound within solid polyvinylpyrrolidone, with solidified cinnamic alcohol adherently distributed therethrough and, in preferred instances, with solidified tannic acid adherently dispersed therewithin, and all in preferred proportions.

12 Claims, No Drawings

IODINE-POLYVINYLPYRROLIDONE SOLID PRODUCT AND METHOD OF PREPARATION

The present invention is concerned with methods of and products for enabling the protecting and storing of active iodine from light and air-exposure deterioration and in solid form, while maintaining the same continuously releasable for active pharmacological use by application of heat and/or moisture; being more particularly directed to adherently bound iodine-polyvinylpyrrolidone solid products and methods of preparing the same.

Underlying the invention, moreover, are discoveries that have apparently eluded prior workers in this art, and, indeed, have been thought to be contraindicated by the prior experience with iodine and polyvinylpyrrolidone. Heretofore, for example, iodine-polyvinylpyrrolidone compositions have been prepared from Lugol's solution or tincture of iodine, or have been formed for aqueous compositions with blended anhydrous sodium bicarbonate stabilizer, as described in U.S. Pat. No. 2,826,532. Other techniques involve mixing elemental iodine and powdered polymeric 1 vinyl 2 pyrrolidone and heating to produce an available iodine-to-iodide ion in the composition of substantially 2-1, as disclosed in U.S. Pat. No. 2,706,701. From the practical point of view, however, these compounds are either only usable in aqueous form, or on wet substrates that must be sealed in metal or other opaque packages to prevent light and air exposure deterioration.

An object of the present invention, on the other hand, is to provide a new and improved method of and product for adherently binding solid iodine within polyvinylpyrrolidone to protect the same from light and air-exposure, while presenting the same as a solid, continuously adapted for immediate release for active pharmacological use by application of heat and/or moisture.

A further object is to provide such a novel product with other adhered bacteriolgical and/or fungicide agents within the solid, all protected from deletereous interaction, and all stored and actively releasable to perform their individual functions.

Other and further objects will be explained hereinafter and are more particularly pointed out in the appended claims. In summary, however, from one of its important aspects, the invention includes a method of protecting and storing active iodine from light and air exposure deterioration and in solid form, while maintaining the same continuously releasable for active pharmacological use by application of heat and/or moisture, that comprises, preparing an alcohol or aqueous solution of finely powdered crystalline iodine; wetting polyvinylpyrrolidone; admixing the iodine solution with the wetted polyvinylpyrrolidone; adding cinnamic alcohol; and drying the mixture to solid state. Preferred additional constituents, including tannic acid may also preferably be adherently bound within the desired product; and other preferred details are also later delineated.

It has been discovered that through the use of cinnamic alcohol (and where fungicidal action is desired, tannic acid) with polyvinylpyrrolidone, in appropriate portions, an unexpected protecting and binding agent for solid iodine can be achieved that enables the novel results of the invention. I have previously used this combination for body temperature and/or moisture release of the action of cinnamic alcohol and tannic acid as described in my prior U.S. Pat. Nos. 3,525,340 and 3,777,016. But these uses were far removed from the surprising discovery that this type of composition, if processed properly, can perform the entirely different function of binding solid iodine, protecting and storing the same against the usual light, heat and air-exposure deterioration, and providing an adherent, bound solid that by slight heat and/or moisture application will automatically release the active iodine for pharmacological use, and the cinnamic alcohol for its bacteriocidal activity and the tannic acid (where used) for its fungicidal properties--all without interaction of these constituents and with the preservation of their individual properties and function.

The further surprise of this discovery will be evident when it is reflected that the art had previously considered that iodine was incompatible with tannic acid (Merck Index, 7th Ed., p. 558, 1960); and when considering the successful application of the product of the invention as adhered to gauze or other dressing or substrates containing starch, the additional fact, as indicated in the above Merck reference, that iodine should also be incompatible with starch. The type of binding of the constituents of the invention enables the solid iodine to be isolated from the tannic acid, if used, and the starch, though intimately admixed and unitarily solidified. More than this, the use of tannic acid in this relationship has also been contraindicated by the teachings of the air, as in the 1960 General Analine Bulletin which, as it now turns out, erroneously indicates that all polyacids cross-link with polyvinylpyrrolidone to form insoluble compounds except in weak alkali.

The novel solid iodine-containing emulsion of the invention, applied, for example, to polyester matting, gauze or foam rubber, serving as a dressing, or on an applicator stick or swab, continuously enables available iodone to be activated when the solid emulsion comes in contact with the moisture and/or slightly elevated body temperature of the skin, blood or blood serum which liquifies the cinnamic alcohol at about 100° F; or when in contact with exogenous moisture, water and/or alcoholic preparations.

In the prior art, as in the first two patents above-mentioned, in the polyvinylpyrrolidone-iodine complex (sold under the General Analine trademark Betadine), the iodine, as before mentioned, is only available in an aqueous medium, or in a propylene-glycol solution in which gauze has been wetted and then immediately packaged and sealed tightly in the wet stage to prevent the complex from drying out and to prevent its exposure to light, heat and air. The same wet propylene-glycol solution, with appropriate packing, is used to maintain the wet stage on an applicator stick or swab. All this is now obviated by the invention which enables an exposably solid dry emulsion to be used with long shelf life.

EXAMPLE 1

A preferred method of protecting solid iodine from light, heat and air-exposure deterioration by binding it in polyvinylpyrrolidone in accordance with the invention, to produce an adherent solid, will now be described.

Polyvinylpyrrolidone K30 (28.349 grams) was dissolved in 19cc of water by agitation, using slow mixing. Finely powdered crystalline iodine (1 gram) was dissolved in 15cc of 95% alcohol (ethanol) and added to the wetted (emulsified) polyvinylpyrrolidone and slowly mixed thoroughly. 2 grams of liquid cinnamic alcohol (solid form melted at about 100° F) was added to the above and slowly agitated. Powdered tannic acid (2 grams) was then added to the above and mixed uniformly therein to form an emulsion. The emulsion was then uniformly spread on a polyester dressing about 36 square inches and was permitted to air-dry at substantially room temperature to evaporate the solvents and moisture and form an adherent unitary solid coating.

In use, placing the coating on a bleeding wound was found to melt the solidified cinnamic alcohol and release active iodine, active anti-bacterial cinnamic alcohol, and independently active fungicidal tannic acid. Tests for the continuous slight heat and/or moisture release of these ingredients were performed, with the following simple visual and olfactory observations demonstrating the above; to wit, rubbing the moist coating on a starch-containing paper shows the purple active iodine, the yellow tannic acid; and the aromatic characteristics of the cinnamic alcohol is also clearly evident.

EXAMPLE 2

The process of Example 1 was repeated with variations of the approximate proportions from the weight percentages therein of: polyvinylpyrrolidone, 82%; cinnamic alcohol, 6%; tannic acid, 9%; and iodine, 3%. These variations showed useful weight proportion ranges of substantially the following: polyvinylpyrrolidone, 82-90%; cinnamic alcohol, 3-15%; tannic acid, 3-12%; and iodine, ½-3%.

EXAMPLE 3

The process of Example 1 was repeated with the finely powdered iodine dissolved in water instead of ethanol, requiring a somewhat longer evaporation and solidifying drying time.

EXAMPLE 4

The process of Example 1, absent the addition of tannic acid.

EXAMPLE 5

The process of Example 1 was repeated but with 1 gram of iodine, 2 grams of cinnamic alcohol, 3 grams of tannic acid and 0.166 grams of hydrocortisone acetate.

In a repetition of Example 5, the iodine was omitted, and a useful hydrocortisone-bound and protected solid coating was achieved.

EXAMPLE 6

The process of Example 1 was repeated, but the emulsion was dried on a ceramic surface and then ground to form a fine dusting powder.

EXAMPLE 7

The process of Example 1 was repeated, with wooden applicator sticks and gauze swabs dipped in the emulsion and dried to form ready applicators.

It has been further found that an effective way of simply varying the percentage of encapsulated or bound solid iodine in the final product, where desired, is to control the amount of alcohol or water solvent above a threshold solubilizing quantity in which the powdered crystals are dissolved.

Further modifications will suggest themselves to those skilled in this art and such are considered to fall within the spirit and scope of the invention as defined in the appended claims.

What is claimed is:

1. A method of making a polyvinylpyrrolidone-iodine composition in which the iodine is stored in solid form protected from light and air-exposure deterioration and is continuously releasable for active pharmacological use by application of at least one of heat and moisture, that comprises, preparing an alcohol or aqueous solution of finely powdered crystalline iodine; forming a solution of polyvinylpyrrolidone; admixing the iodine solution with the polyvinylpyrrolidone solution; adding cinnamic alcohol and thoroughly dispersing the same in the iodine solution-polyvinylpyrrolidone solution; and drying the solution to solid state.

2. The method of claim 1 and in which, following the addition of the cinnamic alcohol but prior to said drying, tannic acid is added to the polyvinylpyrrolidone-iodine solution.

3. The method of claim 1 and in which the solid iodine constitutes substantially ½ to 3% by weight of the solid state product.

4. The method of claim 1 and in which the weight percentages of the constituents are substantially within the ranges: polyvinylpyrrolidone, 82-90%; cinnamic alcohol, 3-15%; and iodine, ½-3%.

5. The method of claim 4 and in which tannic acid is added prior to said drying having substantially a weight percentage range of 3-12%.

6. The method of claim 1 and in which the polyvinylpyrrolidone is in water, and the cinnamic alcohol is added in liquid form.

7. The method of claim 5 and in which the iodine alcohol solvent comprises ethanol.

8. A solid dry polyvinylpyrrolidone-iodine complex comprising about 82-90% polyvinylpyrrolidone, ½-3% iodine, and 3-15% cinnamic alcohol, by weight.

9. The complex of claim 8 and in which the complex comprises about 3-12% tannic acid, by weight.

10. The complex of claim 8 and in which the complex costs a bandage substrate.

11. The complex of claim 8 and in which the complex coats a swab.

12. The complex of claim 8 and in which the complex is powdered.

* * * * *

UNITED STATES PATENT AND TRADEMARK OFFICE
CERTIFICATE OF CORRECTION

PATENT NO. : 4,094,967
DATED : June 13, 1978
INVENTOR(S) : Joseph G. Gilbert

It is certified that error appears in the above-identified patent and that said Letters Patent are hereby corrected as shown below:

Column 4, line 54: "costs" should read -- coats --.

Signed and Sealed this

Fifteenth Day of January 1980

[SEAL]

Attest:

SIDNEY A. DIAMOND

Attesting Officer    Commissioner of Patents and Trademarks